United States Patent
Wong et al.

[11] Patent Number: 5,817,335
[45] Date of Patent: Oct. 6, 1998

[54] OSMOTIC DEVICE WITH HIGH DRUG LOADING AND DELAYED ACTIVATION OF DRUG DELIVERY

[75] Inventors: Patrick S.-L. Wong, Palo Alto; Liang C. Dong, Sunnyvale; Vincent J. Ferrari, San Mateo; Jeri D. Wright; Steven D. Larsen, both of Dublin, all of Calif.

[73] Assignee: ALZA Corporation, Palo Alto, Calif.

[21] Appl. No.: 451,647

[22] Filed: May 26, 1995

[51] Int. Cl.$^6$ ........................................... A61K 9/48
[52] U.S. Cl. .................. 424/453; 424/451; 424/473; 514/962
[58] Field of Search .................. 424/453, 473, 424/451; 514/962; 604/892.1

[56] References Cited

U.S. PATENT DOCUMENTS

| | | | |
|---|---|---|---|
| 3,845,770 | 11/1974 | Theeuwes et al. | 128/260 |
| 3,865,108 | 2/1975 | Hartop | 128/260 |
| 3,995,631 | 12/1976 | Higuchi | 128/260 |
| 4,002,173 | 1/1977 | Manning et al. | 128/296 |
| 4,034,756 | 7/1977 | Higuchi et al. | 128/260 |
| 4,111,202 | 9/1978 | Theeuwes | 128/260 |
| 4,207,893 | 6/1980 | Michaels | 128/260 |
| 4,265,874 | 5/1981 | Bonsen et al. | 424/15 |
| 4,320,759 | 3/1982 | Theeuwes | 128/260 |
| 4,327,725 | 5/1982 | Cortese et al. | 128/260 |
| 4,449,983 | 5/1984 | Cortese et al. | 604/892 |
| 4,595,583 | 6/1986 | Eckenhoff et al. | 424/15 |
| 4,612,008 | 9/1986 | Wong et al. | 604/892 |
| 4,643,731 | 2/1987 | Eckenhoff | 604/892 |
| 4,874,388 | 10/1989 | Wong et al. | 604/891.1 |
| 5,198,229 | 3/1993 | Wong et al. | 424/473 |
| 5,200,195 | 4/1993 | Dong et al. | 424/473 |
| 5,254,349 | 10/1993 | Dong et al. | 424/473 |
| 5,312,388 | 5/1994 | Wong et al. | 604/892.1 |
| 5,312,390 | 5/1994 | Wong | 604/892.1 |
| 5,314,696 | 5/1994 | Paulos | 424/453 |
| 5,417,682 | 5/1995 | Wong et al. | 604/892.1 |
| 5,443,459 | 8/1995 | Wong et al. | 604/892.1 |
| 5,531,736 | 7/1996 | Wong et al. | 604/892.1 |
| 5,558,878 | 9/1996 | Paulos | 424/453 |
| 5,576,019 | 11/1996 | Paulos | 424/453 |

*Primary Examiner*—S. Mark Clardy
*Assistant Examiner*—Robert H. Harrison
*Attorney, Agent, or Firm*—John A. Dhuey; Steven F. Stone

[57] ABSTRACT

The present invention is directed to a fluid-imbibing drug delivery device which is useful for the initial delayed delivery of an active agent formulation to a fluid environment of use, the initial delay period to startup or activation being of a predetermined length of time. The dispensing device is formed of a first and second housing that are in reversibly sliding telescoping arrangement with each other. The first housing contains the active agent formulation and has an aspect ratio less than 1. The housings are preferably ovoloid in shape.

19 Claims, 4 Drawing Sheets

5,817,335

OSMOTIC DEVICE WITH HIGH DRUG LOADING AND DELAYED ACTIVATION OF DRUG DELIVERY

FIELD OF THE INVENTION

The present invention is related to the delayed delivery of an active agent. More particularly, it is related to osmotically-activated devices for dispensing active agents to a biological environment of use following an initial period of delay.

BACKGROUND OF THE INVENTION

Osmotic dispensing devices for delivery of therapeutically active agents are well known in the art. Such devices use an expansion agent to deliver an active agent formulation to an environment of use over a period of hours, days or months. The expansion agent absorbs liquid, expands, and acts to drive out the active agent formulation from the interior of the device in a controlled, usually constant manner. The osmotic expansion agent is used to controllably, usually relatively slowly, and over a period of time, deliver the agent.

Osmotic devices have also been described for prolonged and controlled delivery of one or more active agents where an initial delay of delivery is desired. U.S. Pat. No. 5,198,229, which is incorporated herein by reference, is directed to an osmotic device for delivery of an active agent to the upper gastrointestinal tract. The dispensing device comprises concentric housings that are in slidably telescoping arrangement with each other. A first expansion means imbibes fluid when placed in the stomach environment. This expansion means expands and pushes against a partition layer that in turn pushes against an active agent formulation. The active agent is delivered to the stomach environment through a small exit port in a controlled and continuous manner. After all the active agent has been delivered, the housings separate, the buoyancy chamber is exposed to the stomach environment, thereby increasing the density of the device, and the device sinks and exits out of the stomach.

U.S. Pat. No. 5,312,388, which is incorporated herein by reference, describes the use of slidably telescopic concentric housings in an osmotic device where delivery of more than one active agent is desired or where separate dosings of one active agent are desired. In a particular embodiment, initial rapid delivery of a particular active agent is followed by delayed delivery of the active agent. A loading dose of the active agent is dispensed as soon as the device enters the environment of use. Prolonged delivery is accomplished as a result of an expansion means that imbibes fluid and expands to separate the concentric housings. Upon separation, the active agent contained within the housings is dispensed.

U.S. Pat. No. 5,312,390, which is incorporated herein by reference, describes an osmotic device useful for the initially delayed delivery of an active agent. Slidably telescoping concentric housings separate following absorption of fluid through the housing. A fluid passage means is exposed to the fluid environment and the active agent is expelled in a controlled and continuous manner through an exit port at the end of the housing opposite the fluid passage means.

As can be observed in the above-referenced patents, osmotic devices have been described that provide for an initial pulse of an active agent, that provide for prolonged delivery of an active agent, and that provide for delivery of more than one active agent. However, there remains a continuing need for improved methods and systems for delivering one or more active agents in a reliable and reproducible manner.

SUMMARY OF THE INVENTION

We have observed that devices such as those described above will open in a predictable manner but that the agent contained in the device, depending on its physical forms, is not always immediately released to the environment of use. As a result, the entire dose of drug is not delivered at the desired location and concentration.

Therefore, according to our invention, we have provided an osmotic device that will deliver an active agent following a reproducible period of delay and further will deliver essentially all of the active agent formulation contained within the device at the appropriate time.

Accordingly in one aspect, the invention is directed to a fluid-imbibing delivery device comprising a first housing and a second semipermeable housing that are in reversibly sliding telescoping arrangement with each other. The first housing is preferably adapted to fit within the second housing. The first housing is dimensioned such that its aspect ratio is less than one. The first housing comprises an active agent delivery chamber with at least one active agent formulation and an open end for releasing the active agent formulation. The second housing optionally comprises an expansion chamber with an expansion agent and further optionally comprises a piston.

In another aspect, the invention is directed to a method for delivering essentially all of an active agent formulation following an initial period of no delivery. The method involves placing the above-described device in a fluid environment of use, allowing for fluid to be imbibed through the second housing to expand the expansion agent and separate the first and second housings, and allowing for delivery of essentially all of the active agent formulation to the fluid environment of use.

DESCRIPTION OF THE DRAWINGS

The drawings are not drawn to scale, but are set forth to illustrate various embodiments of the invention. Like numbers refer to like structures.

DETAILED DESCRIPTION OF THE INVENTION

The present invention provides a device which is useful for the delivery of one or more active agent formulations to a fluid environment of use following an initial delay period prior to startup or activation of the device.

Definitions

The phrase "initial delay period", as used herein, intends a predetermined time period such as for greater than from about several minutes to several hours and preferably for a period of from about 30 minutes to about 10 hours.

After the initial delay period, essentially all of the active agent formulation is delivered to the fluid environment of use with the amount of active agent retained in the device minimized. By "essentially all of the active agent formulation" we intend that least about 90% of the active agent formulation is delivered, preferably at least about 95% is delivered and most preferably greater than about 98% of the active agent formulation is delivered to the fluid environment of use. The active agent is preferably administered as a bolus, i.e., once the housings of the device have separated, the dose of agent in the device is released in a short period of time of 1 hour or less and usually within 45 minutes and preferably in less than 30 minutes.

By "high drug loading" is meant that there is little free space between the active agent formulation and the drug delivery vessel. In general, there is less than about 20% by volume, preferably less than about 10% by volume of free space. Free space, that is the space unoccupied by the active agent formulation, enables water from the environment to aid in flushing the drug out of the dosage form. The drug formulation loading of these systems is usually in the range of about 200–1000 mg, and often in the range of 500–750 mg.

As used herein, the terms "therapeutically effective" amount or rate refer to the amount or administtration rate of the active agent needed to effect the desired therapeutic, often beneficial, result.

With reference to the housings of the devices, "impermeable" is meant that the housing is impermeable to both fluids as well as ingredients contained in the dispensing device. By "semipermeable" is meant that the housing is permeable to fluid but impermeable to other ingredients contained in the dispensing device.

Figure 1:
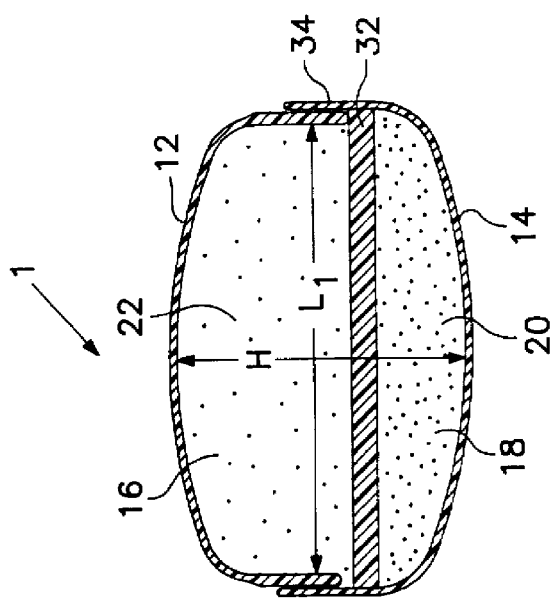
FIG. 1 is a side-elevational view of one embodiment of the delivery device of the present invention, the device being in closed or prepared form prior to placement in the fluid environment of use.

The term "aspect ratio" as shown in FIG. 1 refers to the ratio of the height of the device in closed form designated H, to the long axis $L_1$ of the device ($H/L_1$). $H/L_1$ is less than 1, preferably less than about 0.8 and usually in the range of between about 0.3 to 0.6.

The term "active agent formulation" intends the drug or active agent optionally in combination with pharmaceutically acceptable carriers and additional inert ingredients.

The terms "active agent" and "drug" are used interchangeably herein and refer to an agent, drug, compound, composition of matter or mixture thereof which provides some therapeutic, often beneficial, effect. This includes pesticides, herbicides, germicides, biocides, algicides, rodenticides, fungicides, insecticides, antioxidants, plant growth promoters, plant growth inhibitors, preservatives, antipreservatives, disinfectants, sterilization agents, catalysts, chemical reactants, fermentation agents, foods, food supplements, nutrients, cosmetics, drugs, vitamins, sex sterilants, fertility inhibitors, fertility promoters, microorganism attenuators and other agents that benefit the environment of use. As used herein, the terms further include any physiologically or pharmacologically active substance that produces a localized or systemic effect or effects in animals, including warm blooded mammals, humans and primates; avians; domestic household or farm animals such as cats, dogs, sheep, goats, cattle, horses and pigs; laboratory animals such as mice, rats and guinea pigs; fish; reptiles; zoo and wild animals; and the like. The active drug that can be delivered includes inorganic and organic compounds, including, without limitation, drugs which act on the peripheral nerves, adrenergic receptors, cholinergic receptors, the skeletal muscles, the cardiovascular system, smooth muscles, the blood circulatory system, synoptic sites, neuroeffector junctional sites, endocrine and hormone systems, the immunological system, the reproductive system, the skeletal system, autacoid systems, the alimentary and excretory systems, the histamine system and the central nervous system. Suitable agents may be selected from, for example, proteins, enzymes, hormones, polynucleotides, nucleoproteins, polysaccharides, glycoproteins, lipoproteins, polypeptides, steroids, hypnotics and sedatives, psychic energizers, tranquilizers, anticonvulsants, muscle relaxants, antiparkinson agents, analgesics, anti-inflammatories, local anesthetics, muscle contractants, antimicrobials, antimalarials, hormonal agents including contraceptives, sympathomimetics, polypeptides and proteins capable of eliciting physiological effects, diuretics, lipid regulating agents, antiandrogenic agents, antiparasitics, neoplastics, antineoplastics, hypoglycemics, nutritional agents and supplements, growth supplements, fats, ophthalmics, antienteritis agents, electrolytes and diagnostic agents.

Examples of beneficial agents useful in this invention include prochlorperazine edisylate, ferrous sulfate, aminocaproic acid, mecaxylamine hydrochloride, procainamide hydrochloride, amphetamine sulfate, methamphetamine hydrochloride, benzphetamine hydrochloride, isoproteronol sulfate, phenmetrazine hydrochloride, bethanechol chloride, methacholine chloride, pilocarpine hydrochloride, atropine sulfate, scopolamine bromide, isopropamide iodide, tridihexethyl chloride, phenformin hydrochloride, methylphenidate hydrochloride, theophylline cholinate, cephalexin hydrochloride, diphenidol, meclizine hydrochloride, prochlorperazine maleate, phenoxybenzamine, thiethylperazine maleate, anisindione, diphenadione, erythrityl tetranitrate, digoxin, isoflurophate, acetazolamide, methazolamide, bendroflumethiazide, chlorpropamide, tolazamide, chlormadinone acetate, phenaglycodol, allopurinol, aluminum aspirin, methotrexate, acetyl sulfisoxazole, hydrocortisone, hydrocorticosterone acetate, cortisone acetate, dexamethasone and its derivatives such as betamethasone, triamcinolone, methyltestosterone, 17-β-estradiol, ethinyl estradiol, ethinyl estradiol 3-methyl ether, prednisolone, 17-β-hydroxyprogesterone acetate, 19-norprogesterone, norgestrel, norethindrone, norethisterone, norethiederone, progesterone, norgesterone, norethynodrel, indomethacin, naproxen, fenoprofen, sulindac, indoprofen, nitroglycerin, isosorbide dinitrate, propranolol, timolol, atenolol, alprenolol, cimetidine, clonidine, imipramine, levodopa, chlorpromazine, methyldopa, dihydroxyphenylalanine, theophylline, calcium gluconate, ketoprofen, ibuprofen, cephalexin, erythromycin, haloperidol, zomepirac, ferrous lactate, vincamine, phenoxybenzamine, diltiazem, milrinone, captropril, mandol, quanbenz, hydrochlorothiazide, ranitidine, flurbiprofen, fenbufen, fluprofen, tolmetin, alclofenac, mefenamic, flufenamic, difuninal, nimodipine, nitrendipine, nisoldipine, nicardipine, felodipine, lidoflazine, tiapamil, gallopamil, amlodipine, mioflazine, lisinopril, enalapril, captopril, ramipril, enalaprilat, famotidine, nizatidine, sucralfate, etintidine, tetratolol, minoxidil, chlordiazepoxide, diazepam, amitriptylin, and imipramine. Further examples are proteins and peptides which include, but are not limited to, insulin, colchicine, glucagon, thyroid stimulating hormone, parathyroid and pituitary hormones, calcitonin, renin, prolactin, corticotrophin, thyrotropic hormone, follicle stimulating hormone, chorionic gonadotropin, gonadotropin releasing hormone, bovine somatotropin, porcine somatropin, oxytocin, vasopressin, prolactin, somatostatin, lypressin, pancreozymin, luteinizing hormone, LHRH, interferons, interleukins, growth hormones such as human growth hormone, bovine growth hormone and porcine growth hormone, fertility inhibitors such as the prostaglandins, fertility promoters, growth factors, and human pancreas hormone releasing factor.

It is to be understood that more than one active agent may be incorporated into the active agent formulation in a device of this invention, and that the use of the term "agent" or "drug" in no way excludes the use of two or more such agents or drugs.

The dispensing devices of the invention find use, for example, in humans or other animals. The environment of use is a fluid environment and can comprise the stomach, the intestinal tract, or a body cavity such as the peritoneum or vagina. A single dispensing device or several dispensing devices can be administered to a subject during a therapeutic program.

FIG. 1 depicts, in side-elevational view, a first embodiment of the delivery device according to the present invention. The device is shown in closed or prepared form prior to placement in the environment of use. Dispensing device 1 comprises a first housing 12 and a second housing 14. First housing 12 and second housing 14 are in slidably telescoping arrangement with each other. First housing 12 surrounds and defines an active agent delivery chamber 16 containing an active agent formulation 22.

Second housing 14 encompasses an expansion chamber 18 and contains an expansion agent 20 and a moveable impermeable piston 32.

First housing 12 and second housing 14 are shown to be ovoloid in shape, but they may also be round, hexagonal or any other suitable configuration. First housing 12 and second housing 14 at their ends are close in size and thus a friction fit is formed between the housings. The friction generated is sufficient to maintain the two housings together prior to activation of the expansion agent 20 but not so great as to keep the two housings from sliding apart once an expanding driving force is exerted. The end of first housing 12 is adapted to fit within second housing 14. The bottom edge of the end of first housing 12 provides a platform or ridge 34. Ridge 34 is adapted to receive the driving force of the expansion agent 20, preferably via impermeable piston 32, to effect the separation of the two housings.

In operation, dispensing device 1 is placed in the fluid environment of use and the expansion agent 20 begins to imbibe and absorb fluid through second housing 14 from the environment. The expansion agent 20 expands, exerting a driving force via piston 32 against ridge 34 of first housing 12 to begin to slidably separate first housing 12 from second housing 14. At a predetermined time, first housing 12 and second housing 14 separate apart from each other by the action of the expansion agent 20, via piston 32, on first housing ridge 34. The active agent delivery chamber 16 is exposed to the fluid environment, and the agent formulation 22 is expelled into the environment of use.

Figure 2:
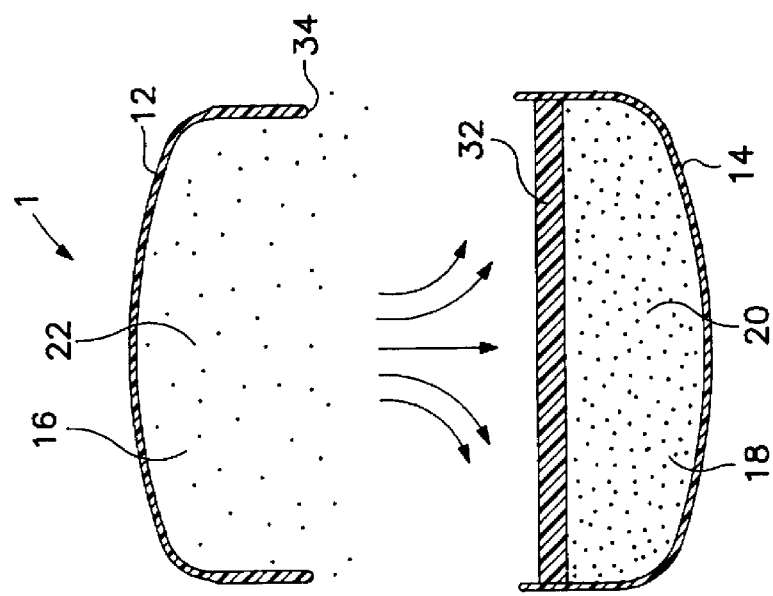
FIG. 2 shows the device of FIG. 1 in operation after placement in the environment of use, showing the expansion chamber expanded and the first and second housings of the device separated.

FIG. 2 shows the dispensing device 1 of FIG. 1 in operation upon separation of the two housings of the device. First housing 12 has been separated from second housing 14 by the expanding driving force of expansion agent 20 on piston 32, which expansion agent 20 has expanded in size as a result of imbibing fluid from the environment. The active agent delivery chamber 16 is exposed to the environment and the active agent formulation 22 is delivered. As described further below, the low aspect ratio permits the entire dose to be delivered immediately upon separation of the housings.

Figure 3:
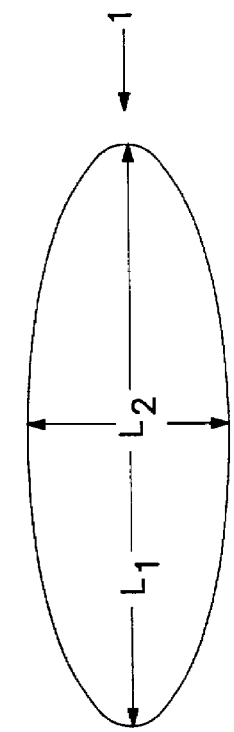
FIG. 3 is a top view of the device of FIG. 1.

FIG. 3 is a top view of first housing 12 of the device 1, showing the long axis $L_1$ and the short axis $L_2$. The length of the long axis L, is greater than the height of the device such that the aspect ratio $(H/L_1)$ is less than 1. The length of the short axis $(L_2)$ is preferably less than the length of the long axis $(L_1)$ such that the ratio of $L_2/L_1$ is less than 1 and usually between about 0.4 and 0.8 and for an oval housing is about 0.5. Design of the device with an aspect ratio of less than 1 allows for a device with high drug loading. The device is further designed to provide sufficient expansion distance prior to separation of the first and second housings to obtain the desired delay period for delivery of the active agent formulation to the fluid environment of use.

Figure 4:
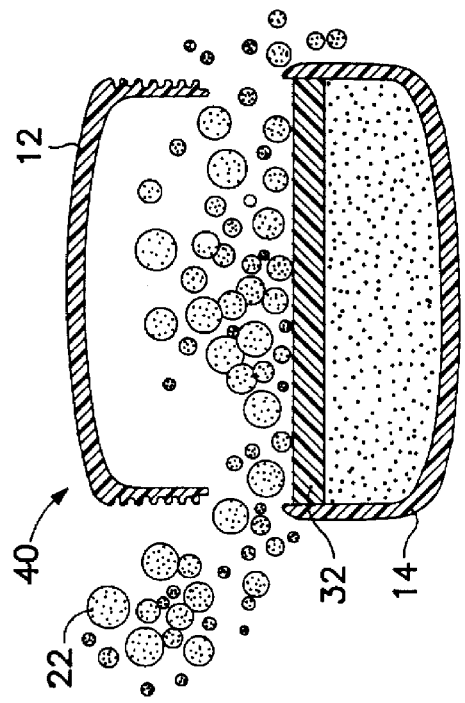
FIG. 4 is side-elevational view of a further embodiment of the delivery device of the present invention, the device being in closed or prepared form prior to placement in the fluid environment.

FIG. 4 is a side-elevational view of a second embodiment of the device of the invention. Similar to FIG. 1, the device 40, shown in closed or prepared form, comprises a first housing 12 and a second housing 14 in slidably telescoping arrangement with each other. The first housing 12 has ridged external walls 42. The interior walls of second housing 14 are smooth and, in the closed form shown in FIG. 4, surround the ridged external walls 42 of first housing 12. These ridged exterior walls increase the drag between the first housing 12 and second housing 14 during expansion thereby increasing the delay period for active agent formulation delivery.

Figure 5:
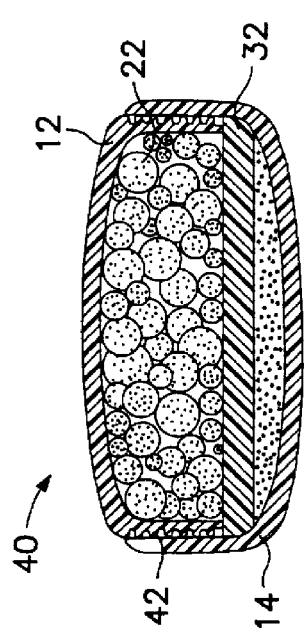
FIG. 5 shows the device of FIG. 4 in operation after placement in the environment of use, showing the expansion chamber expanded and the first and second housings of the device separated.

In operation, dispensing device 40 absorbs fluid through the second housing 14 and the expansion agent 20 expands, exerting a driving force on piston 32 as described with reference to FIG. 1. When the first housing 12 and second housing 14 separate as a result of the force of piston 32 on first housing 12, the active agent formulation 22 is expelled into the environment of use (see FIG. 5).

Figure 6:
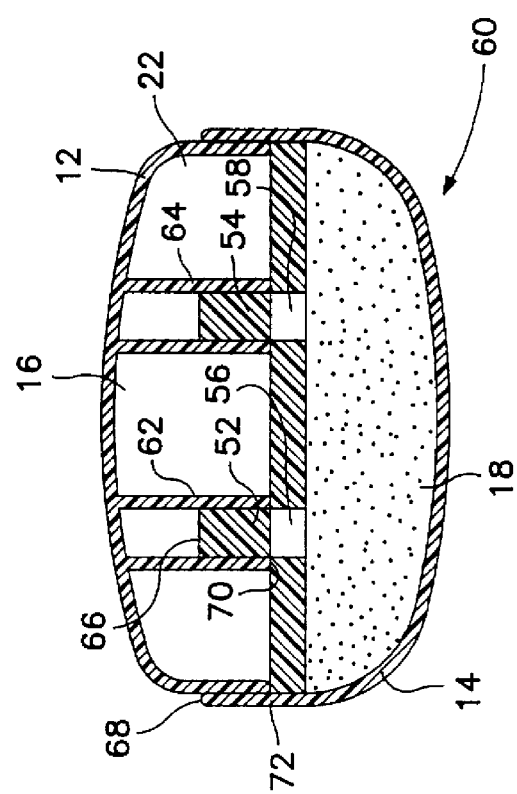
FIG. 6 is a side-elevational view of another embodiment of the delivery device of the present invention in closed form.
Figure 7:
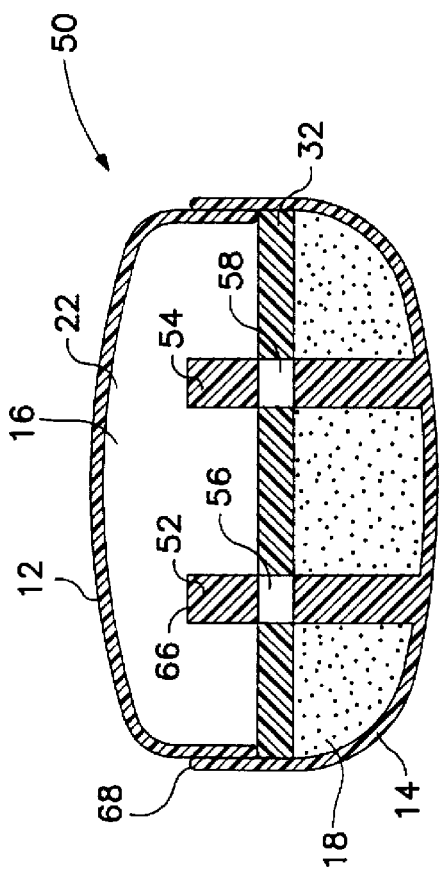
FIG. 7 is a side-elevational view of a further embodiment of the delivery device of the present invention in closed form.

FIGS. 6 and 7 show further embodiments of the device of the invention. Similar to FIGS. 1–5 described above, the dispensing devices 50 and 60 comprise a first housing 12 and a second housing 14 in slidably telescoping arrangement with each other. In these embodiments, posts 52 and 54 are molded into the second housing 14 in order to prevent uneven separation of the first and second housings. FIG. 6 shows holes 56 and 58 for the posts 52 and 54 in the piston 32. In addition to the holes 56 and 58 in the piston 32, FIG.

7 shows receptacles 62 and 64 molded into first housing 12. In operation, holes 56 and 58 (in combination with receptacles 62 and 64 in the embodiment shown in FIG. 7) guide posts 52 and 54 during expansion in order to ensure uniform orientation of housing 12 with respect to housing 14 at all times prior to separation of the housings. As a result of the uniform orientation of the housings and additionally, in view of the drag produced between posts 52 and 54 and the surfaces that surround the posts (holes 56 and 58 in piston 32 and additionally receptacles 62 and 64 in housing 14 of FIG. 7) and the friction produced between housings 12 and 14, the initial period of delay prior to separation of housings 12 and 14 can consistently and reproducibly be accomplished.

Although FIGS. 6 and 7 show the use of two posts for stabilization of the system, the use of any number of posts (two or more) is within the scope of this invention. Posts 52 and 54 are dimensioned so that the top 66 of the posts 52 and 54 will be at essentially the same height as the top 68 of the second housing 14. Further, the top 70 of the receptacles 62 and 64 will be at essentially the same height as the top 72 of the first housing 12.

Figure 8:
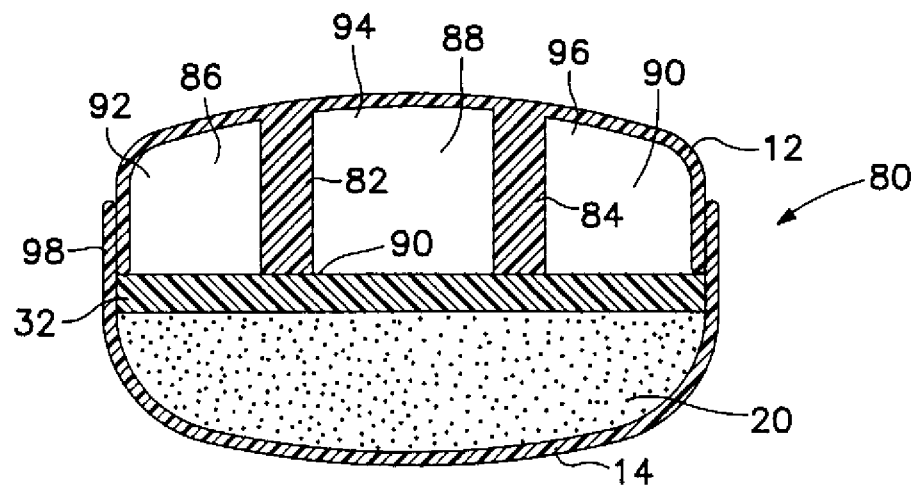
FIG. 8 is a side-elevational view of yet another embodiment of the delivery device of the present invention in closed form.
Figure 9:
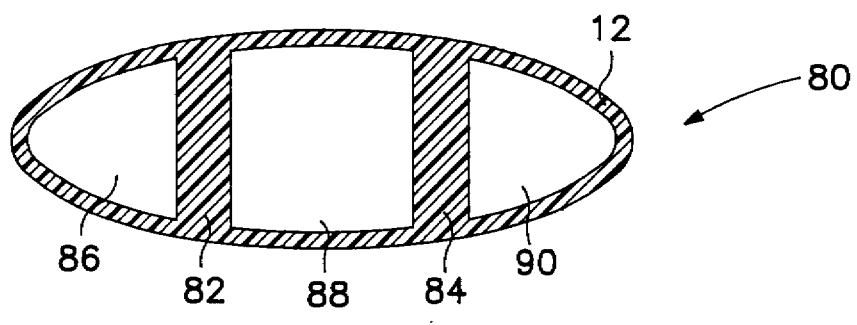
FIG. 9 is a top view of the device of FIG. 8.

FIGS. 8 and 9 are side-elevational and top views, respectively, of the device of yet another embodiment of the invention. The dispensing device 80 comprises a first housing 12 and a second housing 14 in slidably telescoping arrangement with each other as described with regard to FIGS. 1–7 above. In this embodiment, interior walls 82 and 84 are molded into the first housing to provide separate storage compartments 86, 88 and 90 for the storage of multiple drugs or excipient formulations. One or more interior walls may be incorporated into the device, depending on the application. Mutually incompatible drugs or drug/excipient formulations 92, 94 and 96 may be held in these compartments. The height of the interior walls 82 and 84 are dimensioned so that they are firmly in contact with the piston 32 during system operation and storage to prevent hydration or cross-contamination of the formulations 92, .94 and 96. Accordingly, the top 90 of the walls 82 and 84 will be at the same height as the top 98 of the first housing 12. At release, the formulations are exposed to the environment of use at essentially the same time. The walls 82 and 84 provide support surfaces to stabilize movement of the first housing 12 as it is separated from the second housing 14 through contact with the piston 32.

Figure 11:
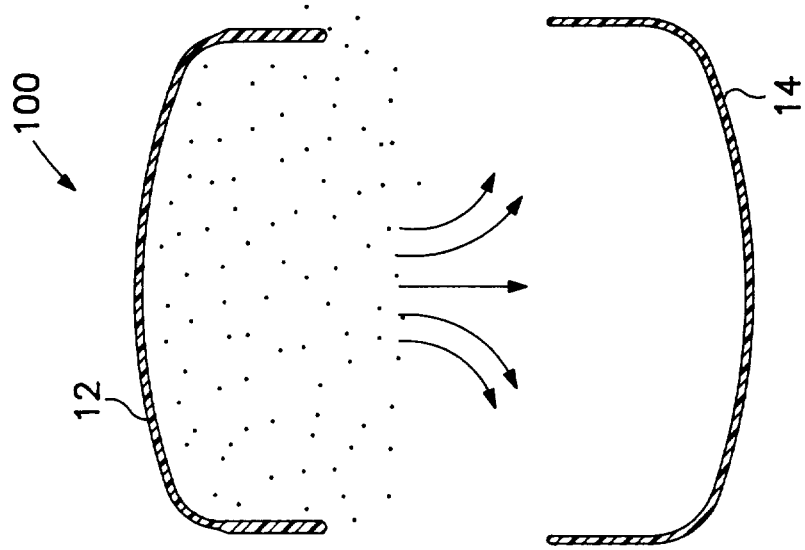
FIG. 11 is a side-elevational view of the device of FIG. 10 in operation after placement in the environment of use, showing the first and second housings of the device separated.
Figure 10:
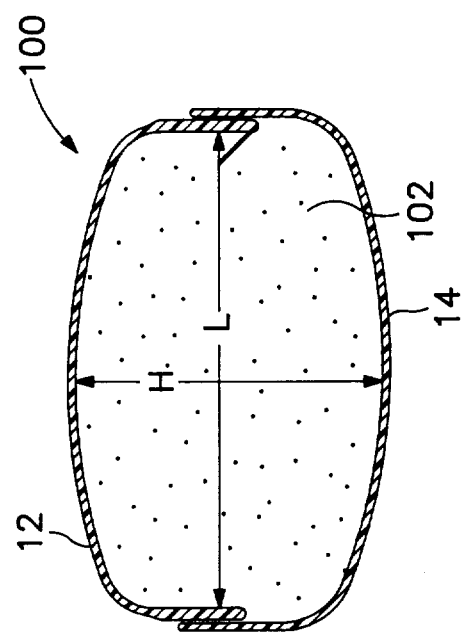
FIG. 10 is a side-elevational view of still another embodiment of the delivery device of the present invention in closed form.

FIGS. 10 and 11 are side-elevational views of the device of still another embodiment of the invention in closed form and following separation of the housings, respectively. The dispensing device 100 comprises a first housing 12 and a second housing 14 in slidably telescoping arrangement with each other. In this embodiment, there is no separate piston or expansion agent. The active agent formulation 102 comprises an active agent and a soluble osmotic agent or hydrophilic disintegrating agent. Examples of soluble osmotic agents include but are not limited to magnesium sulfate, magnesium chloride, sodium chloride, lithium chloride, potassium sulfate, sodium sulfate, mannitol, urea, sorbitol, inositol, sucrose glucose, and the like. Examples of hydrophilic disintegrating agents include but are not limited to crosslinked celluloses (i.e., Ac-Di-Sol™ sodium carboxymethylcellulose, FMC Corp., Philadelphia, Pa.), crosslinked polymers (i.e., crosslinked PVP), and crosslinked starches (i.e., sodium starch glycolate). In this embodiment, both first housing 12 and second housing 14 are semipermeable. Once placed in the fluid environment of use, the active agent formulation imbibes fluid from the environment and swells, pushing apart first housing 12 and second housing 14. The active agent formulation is exposed to the environment upon separation of the first housing 12 and second housing 14. The amount of active agent may be as high as 80 wt % of the active agent formulation. Accordingly, delivery of a large pulse of active agent at a predetermined time is possible.

With reference to the embodiments shown in FIGS. 1–11, first housing 12 must be substantially impermeable in its entirety to the ingress of the external fluid where necessary for substantially protecting the agent or dosage form, or it may be semipermeable. Because first expansion agent 20 operates by imbibing external fluid, and because the active agent formulation 102 in FIGS. 10 and 11 imbibes external fluid, second housing 14 must allow fluid to pass through for activating the expansion agent while being impermeable to the ingredients of the expansion agent. Accordingly, the second housing 14 may be a microporous membrane or a screen, or may be of a composition that is semipermeable, or a combination of these.

Housings 12 and 14 may optionally comprise additional ingredients such as, for example, plasticizers. Impermeable and semipermeable compositions suitable for use in housings 12 and 14, as well as suitable additives, are known in the art, examples of which are disclosed in U.S. Pat. No. 4,874,388, which is incorporated herein by reference.

The delivery device of the present invention is nontoxic, biologically inert, nonallergenic and nonirritating to body tissue, and it maintains its physical and chemical integrity; that is, the device does not erode or degrade in the environment of use during the dispensing period. It is within the scope of the invention that the device be insoluble only during the period of intended use and can thereafter dissolve away in the environment of use. Thus, a dispenser is contemplated which is unaffected by its environment, solubility-wise, at the situs of use or which, alternatively, is only slightly soluble during the period of intended use, such that once its active agent content has been removed it will dissolve or erode away.

The expansion agent or expandable driving agent 20 is nontoxic, nonallergenic and biologically inert. In one embodiment, agent 20 comprises an osmopolymer. Osmopolymers interact with water and aqueous biological fluids and swell or expand to an equilibrium state. Osmopolymers exhibit the ability to swell in fluid and to retain a significant portion of the imbibed and absorbed fluid within the polymer structure. The expansion agent 20 in another embodiment is an osmagent. Osmagents are also known as osmotically effective solutes or compounds. Osmagents that can be used for the purpose of this invention include inorganic and organic compounds that exhibit an osmotic pressure gradient across a semipermeable, i.e., a fluid-permeable wall. The expansion agent 20 in yet another embodiment is an osmagent dispersed within an osmopolymer. The expansion agent can be a tablet or a layer, or a plurality of tablets or layers, and can be placed into position in the device or it can be pressed into the device. The osmagent or osmopolymer can be in any suitable form such as particles, crystals, pellets, granules, and the like, when pressed into a tablet layer or into the device. Osmagents and osmopolymers are known in the art and are described in, for example, U.S. Pat. Nos. 3,865,108, 4,002,173, 4,207,893, 4,327,725 and 4,612,008 which are incorporated herein by reference.

Piston 32 is substantially impermeable to the passage of fluid, and serves to restrict the passage of fluid present in the expansion agent into the first housing. It operates to essentially maintain the integrity of the active agent formulation 22 and the expansion agent 20. Additionally, and importantly, piston 32 acts to insure that the expanding driving force generated by the expansion agent 20 is applied directly against first housing 12 to effect the separation of the first and second housings. Thus, piston 32 must be of sufficient strength, thickness and rigidity to transfer the driving force against first housing 12.

Representative impermeable materials useful as piston 32 are known in the art and are described in, for example, U.S. Pat. No. 4,874,388 which is incorporated herein by reference.

The active agent formulation comprises the active agent to be delivered, as a liquid, solid, semisolid or thermosensitive composition, generally in a carrier substance and with or without additional inert ingredients. The active agent formulation may additionally include dosage forms containing the active agent which are capable of maintaining their physical configuration and chemical integrity while housed within the dispenser. These include, without limitation, tablets with or without a density element; matrix tablets; spheres; pellets and elongated tablets; capsules; elementary osmotic pumps, such as those described in U.S. Pat. No. 3,845,770; mini-osmotic pumps, such as those described in U.S. Pat. Nos. 3,995,631, 4,034,756 and 4,111,202; and multichamber osmotic systems referred to as push-pull and push-melt osmotic pumps, such as those described in U.S. Pat. Nos. 4,320,759 and 4,449,983; all of which patents are incorporated herein by reference.

The pharmaceutically acceptable carrier useful herein may include more than one ingredient, such as, for example, buffers, viscosity regulating vehicles, surfactants, dyes, permeation enhancers, proteinase inhibitors, or other formulation ingredients and additives, as are known in the art. The carrier may contain more than one active agent. The active agent formulation can erode or disintegrate and can be in the form of a wax formulation, a solid core or a tablet, for example. The formulation can immediately dissolve upon exposure to fluid or it may erode slowly with or without the presence of excipients for controlling erosion.

The active agent formulation can be designed in a multitude of ways to provide a specific drug delivery profile. One embodiment may comprise a formulation that contains a biologically acceptable solid surfactant which is capable of slow dispersion in the environmental fluid. In another embodiment, the formulation may contain a fluid-insoluble wax and a surfactant so that the formulation is susceptible to erosion in the environment. In still another embodiment, the formulation may be effervescent and provide drug delivery in a finely dispersed form. This is accomplished by the addition of a solid basic compound capable of evolving carbon dioxide in the presence of an acid in the environment of use. Suitable basic compounds are disclosed in U.S. Pat. No. 4,265,874 which is incorporated herein by reference. In a further embodiment, the formulation may include an osmotic agent or solute, such as those described above with reference to the expansion agent, so that when the formulation comes into contact with the environmental fluid, it immediately dissolves. In yet another embodiment, the agent formulation can be comprised of an agent and a thermoresponsive composition. In this manner, the formulation would exhibit solid-like properties at room temperature of 21° C. and within a few degrees Celsius thereof, and would have a melting point that approximates mammalian body temperatures of 37° C. and within a few degrees Celsius thereof. The term "thermoresponsive" as used herein denotes the physical-chemical property of an agent carrier composition to exhibit solid, or solid-like properties at temperatures up to 31° C. and become fluid, semi-solid or viscous when disturbed by heat at temperatures from 31° C., usually in the range of 31° C. to 45° C. Suitable materials useful as active agent carriers and excipients are known in the art and are disclosed in U.S. Pat. Nos. 4,595,583 and 4,874,388, for example which are incorporated herein by reference.

The agents can be in various forms, such as uncharged molecules, components of molecular complexes or nonirritating, pharmacologically acceptable salts. Also, simple derivatives of the agents (such as ethers, esters, amides, etc) which are easily hydrolyzed by body pH, enzymes, etc, can be employed.

The amount of active agent employed in the delivery device will be that amount necessary to deliver a therapeutically effective amount of the agent to achieve the desired result at the site of delivery. In practice, this will vary widely depending upon the particular agent, the site of delivery, the severity of the condition, and the desired therapeutic effect. Thus, it is not practical to define a particular range for the therapeutically effective amount of active agent incorporated into the device.

For proper delivery of the active agent, it may be desirable in some instances for the dispensing device to delivery active agent to a particular environment of use. Thus, it may be necessary for the device to remain in a particular environment of use until such time as the agent formulation has been delivered or, alternatively, for the device to pass through one particular environment to another prior to delivering the agent formulation. In such cases, additional elements are included in the device, or the device is designed in such a way to provide for such particular delivery. For example, when the environment of use is the rumen of a ruminant animal, a density element may be included in the dispensing device so that the device is weighted to remain within the rumen during the dispensing period. Density elements are known in the art and are discussed in, for example, U.S. Pat. No. 4,874,388 which is incorporated herein by reference. When the environment of use is the human stomach, it may be desirable for the device to, for example, have a low initial density or to include air in that portion of the internal compartment of the device that also contains the agent formulation. In this manner, the device will float on the surface of the stomach contents and remain in the stomach until the device opens to release the formulation. Where it is desirable, on the other hand, to delay the release of an active agent which, for example, is inactivated by the stomach contents or may cause nausea or bleeding by irritating the gastric mucosa so that delivery in the stomach is not desired, an enteric coating can be applied over at least that portion of the housing of the dispensing device that is comprised of a semipermeable membrane. Enteric coatings will remain intact in the stomach but will rapidly dissolved once they arrive at the small intestine, thereafter allowing fluid to be imbibed to activate the dispensing device. Enteric coatings are well known in the art and are discussed at, for example, "Remington's Pharmaceutical Sciences", Mack Publishing Co., Easton, Pa.

The total delay time prior to separation of the two housings of the dispensing device and the total delivery time of the active agent formulation can be controlled by a number of means to provide a sharp start-up of delivery at a particular time with high accuracy. For example, the rate of fluid imbibition into the expansion agent, and thus the rate of expansion of the agent, can be controlled by the particular choice of semipermeable membrane or microporous screen.

The rate of expansion of the expansion agent can also be controlled by the choice of composition of the expansion agent. The distance of overlap between the telescoping portions of the first and second housings can determine the period of time required for the two housings to separate. Combinations of such control means may be used. Such control means are known in the art and can be determined without undue experimentation.

The delivery device of the present invention can be manufactured by standard manufacturing techniques. For example, in the preparation of devices of the present invention, first housing 12 (the vessel) and second housing 14 (the cap) may be separately molded or extruded to the desired shape. Possible semipermeable materials from which the second housing 14 may be prepared include, for example, water flux enhanced Hytrel® polyester elastomers (Du Pont), cellulose esters, water flux enhanced ethylene-vinyl acetate copolymers, semipermeable membranes made by blending a rigid polymer with water-soluble low molecular weight compounds, and other semipermeable materials known in the art. Impermeable materials from which the first housing 12 may be prepared include, for example, polyethylene, polystyrene, ethylene-vinyl acetate copolymers, Hytrele polyester elastomers (Du Pont) and other impermeable materials known in the art.

The device can be assembled as follows. Active agent formulation 22 is placed in first housing 12 at its end opposite the exit means, which end is initially open; the formulation may be in the form of a liquid, solid, semi-solid, powder or shaped tablet or tablets, for example. A "bilayer osmotic plug" composed of impermeable piston 32 and first osmotic layer or expansion agent 20 is prepared in a shape that will fit within second housing 14. The piston 32 and expansion agent 20 are compressed into a tablet on a rotary bilayer tablet press. The bilayer osmotic plug is placed within the second housing 14 and the assembly is placed over the end of the filled first housing 12 so that piston 32 is adjacent to the active agent formulation 22 to give a device as illustrated in FIG. 1.

When the device of the invention has the configuration of FIG. 6, it may be prepared by separately molding the first housing 12 and second housing 14 into their desired shapes as described above, however, two or more posts are molded into the second housing 14. Holes are then punched into the push plate to concentrically surround the posts such that the posts can pass through the piston to enter the active agent delivery chamber 16. However, a friction fit between the two posts and holes should be ensured to prevent cross-contamination of the active agent formulation 22 and expansion chamber 18. The device is assembled as described above.

When the device of the invention has the configuration of FIG. 7, it may again be prepared by separately molding the first housing 12 and second housing 14 into their desired shapes. Two or more posts are molded into the second housing 14. Holes are punched into the piston to concentrically surround the posts and to provide a friction fit between the posts and the holes. Two or more receptacles are further molded into the first housing 12 to concentrically surround the posts such that the receptacles engage the posts prior to separation of the first and second housings.

When the device of the invention has the configuration of FIG. 8, it may be prepared by separately molding the first housing 12 and second housing 14 into their desired shapes. One or more walls are molded into first housing 12 to provide separate active agent formulation compartments. This further increases the surface area of the first housing in contact with the second housing, thereby allowing for a more even distribution of force across the first housing 12. The same or different active agent formulations may be placed in the two or more compartments of first housing 12. The device is finally assembled as described above.

In the case of the device of FIGS. 10 and 11, the assembly of the device is carried out in a similar fashion as described in FIG. 1, but the piston and expansion agent are omitted.

The following examples are intended to illustrate but not to limit the invention.

EXAMPLE 1

A delivery device according to the present invention is prepared as follows.

The bilayer osmotic plug portion of the device is a compressed bilayer tablet composed of 200 mg of a polymeric osmotic formulation (expansion agent) and a 200 mg wax-based push plate.

The polymeric osmotic formulation has a composition of 59.5 wt % polyethylene oxide (Polyox® 303, Union Carbide), 29 wt % sodium chloride, 5 wt % polyacrylic acid (Carbomer® 934P, B. F. Goodrich), 5 wt % hydroxypropylmethylcellulose E-5 (Aqualon) and 1 wt % ferric oxide. Each of the above components was screened through a 40 mesh screen. The sized components were added to a mixing vessel and mixed thoroughly for 10 minutes. Ethanol was slowly added while mixing until a wet mass was formed. The wet mass was screened through a 20 mesh screen, and the wet granules were allowed to air dry for 18 hours. After drying, the granules were rescreened through a 20 mesh screen. Magnesium stearate (0.5 wt %) was added to the granulation and the granulation was mixed thoroughly for 5 min.

The push plate has a composition of 95 wt % microcrystalline wax (MF-2JH Durawax®, Astor Wax Corp.) and 5 wt % gelatin (Type A, 250–300 bloom, Knox Gelatin). Each component was screened through a 40 mesh screen before being added to a mixing vessel. The dry materials were then mixed thoroughly for 10 minutes, after which purified water was slowly added to the mixture while stirring was continued. After a wet mass was formed, the mixture was passed through a 20 mesh screen, and the granules were oven-dried at 40° C. for 24 hours. The granules were dried and were rescreened through a 20 mesh screen.

The osmotic formulation (200 mg) and the wax push plate formulation (200 mg) were compressed in a rotary press into a bilayer tablet. The osmotic face of the tablet is convex, to conform to the shape of the device, while the push plate face of the tablet is flat. Tabletting was conducted to produce a clean, distinct interface between the two layers.

The vessel portion (first housing) of the device, with one closed and one open end, was prepared by placing the polyethylene in an extruder with a barrel temperature of 130° C. and extruding the material into a mold for the vessel. The polyethylene was allowed to cool in the mold, after which the finished vessel was removed.

To prepare the cap portion (second housing) of the device, 59.5 wt % polycaprolactone (Tone 787, Union Carbide), 25.5 wt % polyethylene oxide (Polyox Coagulant, Union Carbine) and 15% polyethylene glycol were thoroughly mixed together and the mixture was added to the hopper of a screw mixer to form pellets. The polymeric pellets were heated at 127° C. and injection molded to form the cap. The polymer mixture was allowed to cool after injection into the mold, after which the cap was removed.

The delivery device is assembled as follows. The desired active agent formulation is placed into the vessel. Next, an osmotic engine bilayer tablet is placed into the completed cap, with the convex osmotic layer pointed into the closed end of the cap and the push plate exposed toward the cap opening. The open end of the filled vessel is fitted inside the open end of the cap, and the two pieces are compressed together until the cap, osmotic bilayer tablet and vessel fit together tightly. The length of the long axis ($L_1$) is 0.740 inches. The length of the short axis ($L_2$) is 0.339 inches. The height of the bilayer osmotic portion of the device is 0.134 inches and the overall height of the device (H) is 0.375 inches. The aspect ratio ($H/L_1$) is 0.501 and the ratio of the short axis to the long axis ($L_2/L_1$) is 0.458. When the delivery device is placed into the environment of use, the osmotic bilayer causes expansion of the cap and delivery of active agent formulation following separation of the cap and the vessel.

EXAMPLE 2

Delivery devices are prepared as described in Example 1 but contain no active agent formulation. The molds used for the first and second housings allowed for the preparation of devices with aspect ratios of 0.501, and for configurations as follows: (1) smooth external walls; (2) ridged external walls on the first housing; (3) smooth external walls and internal posts; and (4) smooth external walls and walled compartments.

The opening times of the devices were measured as follows. The devices are placed in artificial intestinal fluid (USPXIX, intestinal fluid, simulated, TS; modified by not including enzymes). A plastic rod was glued onto the drug vessel portion of the device. The opening time was determined to be the time interval at which the osmotic engine cap separated from the drug vessel. The opening times of each of the devices is about 6.5 hours after placement into the intestinal fluid.

EXAMPLE 3

A device for the delivery of acetaminophen taken at 10 PM and delivered 6–8 hours later to avoid morning asthmatic pain is prepared as follows. 59.5 wt % polycaprolactone (Tone 787, Union Carbide), 25.5 wt % polyethylene oxide (polyox coagulant, Union Carbide) and 15 wt % polyethylene glycol were thoroughly mixed. The mixture was added to the hopper of a screw mixer to form pellets. The polymeric pellets were heated to 127° C. and injection molded to form both the cap and the vessel portions of the device. The polymer mixture was allowed to cool after injection into the molds, after which the cap and vessel were removed.

The delivery device is assembled as follows: 500 mg acetaminophen and 500 mg PVPXL (International Specialty Products) are placed into the vessel. The open end of the filled vessel is fitted inside the open end of the cap and the two pieces are compressed together to fit tightly. The device has an aspect ratio of 0.365. In this case, the PVPXL serves as the osmotic agent.

Modifications of the above-described modes for carrying out the invention that are obvious to persons of ordinary skill in the related arts are intended to be within the scope of the following claims.

What is claimed is:

1. A fluid-imbibing delivery device for dispensing essentially all of an active agent formulation to a fluid environment of use after an initial, preset delay of startup of delivery, the device comprising:

(a) a first and a second housing, the first and second housings having an open end and a closed end, the first and second housings being releasably joined adjacent their open ends, the second housing being semipermeable;

(b) an active agent formulation comprising at least one active agent within said first housing; and (c) means associated with said first and second housings for separating said first and second housings after an initial time period;

wherein the device is dimensioned such that the ratio of the height to the long axis is less than one.

2. The device of claim 1 wherein the first housing is impermeable.

3. The device of claim 1 wherein said separating means comprises an expansion agent selected from the group consisting of osmagents, osmopolymers and mixtures thereof within the second housing.

4. The device of claim 3, further comprising a piston disposed between said expansion agent and said active agent formulation.

5. The delivery device of claim 1, wherein the housings are ovoloid in shape.

6. The delivery device of claim 1, wherein the active agent formulation is selected from the group consisting of liquid, solid, semi-solid thermo-responsive formulations and mixtures thereof.

7. The delivery device of claim 1, wherein at least a portion of the external wall of the first housing is ridged.

8. The delivery device of claim 4, wherein the second housing further comprises two posts and wherein the piston comprises a push plate with two holes for receiving the posts therethrough.

9. The delivery device of claim 8, wherein the first housing further comprises two receptacles, each of said receptacles designed to concentrically surround each of said second housing posts.

10. The delivery device of claim 2, wherein the first housing further comprises an impermeable wall that separates the first housing into two sections.

11. The delivery device of claim 10, wherein the impermeable wall bisects the long axis of the first housing.

12. The delivery device of claim 10, wherein each of the two sections of the first housing contains a different active agent formulation.

13. The device of claim 10 wherein each of the two sections of the first housing contains the same active agent.

14. The device of claim 1 which is further dimensioned such that the ratio of the length of the short axis to the length of the long axis is less than one.

15. The device of claim 1 that further comprises an enteric coating.

16. The device of claim 1 wherein the first housing is semipermeable.

17. The device of claim 16 wherein the active agent formulation comprises a soluble osmotic agent.

18. The device of claim 16 wherein the active agent formulation comprises a hydrophilic disintegrating agent.

19. A method for delivering essentially all of an active agent formulation contained in a delivery device to a fluid environment after an initial preset delay of startup of delivery, said method comprising:

(a) placing a fluid-imbibing delivery device into the fluid environment, said device comprising:

(i) a first housing and a second housing, the first and second housings having an open end and a closed end, the first and second housings being releasably joined adjacent their open ends, the second housing being semipermeable;
(ii) an active agent formulation comprising at least one active agent within said first housing;
(iii) means associated with said first and second housings for separating said first and second housings after an initial time period;

wherein the device is dimensioned such that the ratio of the height to the long axis is less than one;
(b) allowing fluid to be imbibed through at least a portion of the second housing thereby separating said first and second housings to expose the active agent formulation to the fluid environment; and
(c) allowing for delivery of essentially all of the active agent formulation to the fluid environment of use.

* * * * *